(12) United States Patent
Jimoh

(10) Patent No.: US 6,689,719 B2
(45) Date of Patent: Feb. 10, 2004

(54) COFORMULATION OF CARFENTRAZONE-ETHYL AND GLYPHASATE

(75) Inventor: Ganiyu A. Jimoh, St. Louis, MO (US)

(73) Assignees: Monsanto Technology LLC, St. Louis, MO (US); FMC Corporation, Philadelphia, PA (US)

(*) Notice: Subject to any disclaimer, the term of this patent is extended or adjusted under 35 U.S.C. 154(b) by 0 days.

(21) Appl. No.: 10/075,337

(22) Filed: Feb. 14, 2002

(65) Prior Publication Data

US 2002/0183206 A1 Dec. 5, 2002

Related U.S. Application Data

(63) Continuation-in-part of application No. 09/633,193, filed on Aug. 4, 2000, now Pat. No. 6,369,001.
(60) Provisional application No. 60/269,193, filed on Feb. 15, 2001, provisional application No. 60/331,348, filed on Feb. 14, 2001, and provisional application No. 60/148,423, filed on Aug. 11, 1999.

(51) Int. Cl.[7] .................. A01N 25/22; A01N 43/653; A01N 57/02
(52) U.S. Cl. ............... 504/128; 504/206; 504/273
(58) Field of Search ............... 504/128, 206, 504/273

(56) References Cited

U.S. PATENT DOCUMENTS

| | | |
|---|---|---|
| 4,818,275 A | 4/1989 | Theodoridis |
| 4,975,110 A | 12/1990 | Puritch et al. |
| 5,096,711 A | 3/1992 | Dookhith et al. |
| 5,098,467 A | 3/1992 | Puritch et al. |
| 5,106,410 A | 4/1992 | Puritch et al. |
| 5,125,958 A | 6/1992 | Poss |
| 5,206,021 A | 4/1993 | Dookhith et al. |
| 5,217,520 A | 6/1993 | Poss |
| 5,565,409 A | 10/1996 | Sato et al. |
| 5,928,995 A | 7/1999 | Lichtner, Jr. |
| 5,935,905 A | 8/1999 | Mito |
| 5,990,045 A | 11/1999 | Leep et al. |
| 6,117,816 A | 9/2000 | Jimoh et al. |
| 6,127,318 A | 10/2000 | Sato et al. |
| 6,165,939 A | 12/2000 | Agbaje et al. |

FOREIGN PATENT DOCUMENTS

| | | |
|---|---|---|
| EP | 0 485 207 A1 | 11/1991 |
| EP | 0 617 894 A1 | 1/1994 |
| EP | 0 617 894 A1 | 10/1994 |
| GB | 2 267 825 | * 12/1993 |
| JP | 7-89817 | 4/1995 |
| JP | 10045516 | 2/1998 |
| WO | WO 90/07277 A1 | 7/1990 |
| WO | WO 96/34528 | 11/1996 |
| WO | WO 97/38581 | 10/1997 |
| WO | WO 97/41730 | 11/1997 |
| WO | WO 98/12923 | 4/1998 |
| WO | WO 98/54967 | 12/1998 |
| WO | WO 99/27781 | 6/1999 |
| WO | WO 99/40785 | 8/1999 |
| WO | WO 99/45780 | 9/1999 |
| WO | WO 99/51099 | 10/1999 |
| WO | WO 99/57965 | 11/1999 |
| WO | WO 99/57966 | 11/1999 |
| WO | WO 99/65314 | 12/1999 |
| WO | WO 00/08932 | 2/2000 |
| WO | WO 00/08935 | 2/2000 |
| WO | WO 00/08936 | 2/2000 |
| WO | WO 00/78139 | 12/2000 |
| WO | WO 01/52650 | 7/2001 |
| WO | WO 01/70024 | 9/2001 |

OTHER PUBLICATIONS

Devine, M., et al., Section 8.4, Inhibitors of Protoporphyrinogen–Oxidase, *Physiology of Herbicide Action*, 1993, pp. 152–156, P T R Prentice Hall, Englewood Cliffs, New Jersey.

International Search Report from the European Patent Office mailed Dec. 3, 2002.

International Search Report from the European Patent Office mailed Oct. 30, 2002.

* cited by examiner

*Primary Examiner*—S. Mark Clardy
(74) *Attorney, Agent, or Firm*—Senniger, Powers, Leavitt & Roedel; Joseph A. Schaper

(57) ABSTRACT

A stable, liquid concentrate herbicidal microemulsion composition is provided. The composition comprises N-(phosphonomethyl)glycine or a salt thereof in a continuous aqueous phase and carfentrazone-ethyl in a discontinuous oil phase.

45 Claims, No Drawings

COFORMULATION OF CARFENTRAZONE-ETHYL AND GLYPHASATE

CROSS REFERENCE TO RELATED APPLICATIONS

This application claims the benefit of U.S. Provisional Application Serial No. 60/269,193 filed Feb. 15, 2001 and U.S. Provisional Application Serial No. 60/331,348 filed Feb. 14, 2001 and is a continuation-in-part of U.S. patent application Ser. No. 09/633,193 filed Aug. 4, 2000, which claims priority from U.S. Provisional Application Serial No. 60/148,423 filed Aug. 11, 1999.

FIELD OF THE INVENTION

The present invention relates to compositions useful in agriculture comprising at least two herbicidal active ingredients, one of which is an oil-soluble herbicide and the other of which is a water-soluble herbicide. More particularly, the present invention relates to stable liquid concentrate compositions of such herbicidal active ingredients.

BACKGROUND OF THE INVENTION

As a means of killing or otherwise controlling unwanted plants, e.g., weeds, in agriculture and related endeavors, it is desirable to treat such plants or the locus thereof with chemical herbicides. A common method of herbicidal treatment in agricultural endeavors is to treat a field to remove or control unwanted vegetation as preparation for planting a crop plant, a method otherwise known as "burndown." However, single herbicides typically lack the weed control spectrum, e.g., the range of weed species effectively controlled by the herbicide, to fully control the diversity of weeds in a field. Therefore, it is common to apply two or more herbicides simultaneously in order to achieve the desired spectrum of control. To facilitate the simultaneous application of two or more herbicides, it is common to package the different herbicides separately as concentrate formulations, which can be admixed with water in a spray tank by the end user, a method also known as tank-mixing. More conveniently, however, the different herbicides can be coformulated in a single concentrate formulation, requiring only dilution in water by the end user prior to application by spraying. Such a formulation is often known as a package-mix.

Further, applying combinations of two or more herbicides simultaneously to a field may be necessary or desired for synergistic effects other than an increased control spectrum. For example, many water-soluble herbicides such as N-(phosphonomethyl)glycine have prolonged visual symptomology, that is, it takes a relatively long period of time (i.e., up to two weeks or more) for susceptible plants to show the visual effects of treatment. Generally, such extended periods without any visual indication of herbicidal effectiveness detracts from the commercial value of a herbicidal product. Therefore, it is often beneficial to combine two or more herbicides in a tank mix or a package-mix that will provide for more rapid burndown and earlier visual symptomology, thus improving the value of the overall herbicidal product.

Package-mix formulations present numerous challenges to the formulator of agricultural chemicals such as herbicides. For example, the formulation should contain the herbicidal active ingredients at as high a total concentration as possible, for maximum convenience to the end user and to minimize packaging and shipping costs, while keeping the active ingredients within the desired weight ratios with respect to each other. Most importantly, the package-mix formulation must exhibit sufficient physical and chemical stability to have an effective shelf life of at least a few months, preferably at least a year, and ideally at least two years.

Where the package-mix formulation contains a first herbicide that is oil-soluble and that undergoes chemical degradation, even at a slow rate, in water, and a second herbicide that is water-soluble, the challenge of providing a storage-stable liquid concentrate formulation is particularly acute. Water used as the solvent for the second herbicide acts as a degradation medium for the first herbicide. Typically, hydrolysis is the most common water-mediated degradation mechanism; however, package-mix formulations with chemically unstable active ingredients are also subject to oxidation, dehalogenation, bond cleavage, Beckmann rearrangement and other forms of degradation.

Liquid concentrate coformulations of two herbicidal active ingredients, one of which is water-soluble and the other of which is oil-soluble, are known in the art in the form of emulsions, most commonly oil-in-water type emulsions having a discontinuous oil phase dispersed in a continuous aqueous phase with the aid of one or more emulsifying agents. The water-soluble active ingredient is contained predominantly in the aqueous phase and the oil-soluble active ingredient is contained predominantly in the oil phase. The individual oil particles can be large enough to interfere with the transmission of light, giving rise to a cloudy or milky emulsion known as a macroemulsion. However, where the individual oil particles are so small as to allow light to be transmitted without noticeable scattering, the emulsion is clear, i.e., transparent, and is known as a microemulsion. Microemulsions offer a number of practical advantages, one of the most important being that they typically remain homogeneous without agitation for long periods of time. In this respect, a microemulsion formulation can be handled by an agricultural technician or other user with the same ease and convenience as a simple aqueous solution. However, selecting excipient ingredients for the preparation of a microemulsion is not necessarily straightforward or easy.

Difficulties in preparing stable microemulsions suitable for effective weed control and good crop safety are compounded when the active ingredients to be coformulated are a water-soluble herbicide and an oil-soluble herbicide. For example, one challenge is that water-mediated chemical degradation, e.g., hydrolysis, of the oil-soluble herbicide must be minimized. Minimizing hydrolysis is especially difficult in microemulsions, where the oil particles containing the oil-soluble herbicidal active are extremely small and therefore present a very large interfacial area with the aqueous phase.

Another challenge is that microemulsions must contain surfactants, which tend to facilitate transfer of the oil-soluble herbicidal active across the large interface between the oil and aqueous phases, increasing the potential for chemical degradation. However, surfactants are important to the microemulsion composition, functioning as emulsifying agents to physically stabilize the microemulsion, as dispersants to prevent aggregation of oil particles when the microemulsion is diluted in water for application to plants, and as adjuvants to enhance herbicidal efficacy of one or both active ingredients, for example by improving retention on or adhesion to foliar surfaces of the applied composition or by improving penetration of the active ingredient(s) into or through the cuticles of the plant foliage.

SUMMARY OF THE INVENTION

Among the several features of the invention, therefore, may be noted the provision of a novel liquid concentrate herbicidal composition useful in agriculture wherein at least two herbicidal active ingredients, one of which is an water-soluble herbicide and the other of which is an oil-soluble herbicide, can be coformulated; the provision of such a novel composition comprising a continuous aqueous phase having a discontinuous oil phase dispersed therein; the provision of such a novel composition having a broader weed control spectrum; the provision of such a novel composition that exhibits rapid burndown and early visual symptomology; the provision of such a novel composition that allows for higher loading of herbicidal active ingredients; and the provision of such a novel composition which has prolonged storage stability and is relatively easy to use.

Briefly, therefore, the present invention is directed to a liquid concentrate herbicidal microemulsion composition having a continuous aqueous phase and a discontinuous oil phase. The composition comprises an herbicide comprising N-(phosphonomethyl)glycine or a salt thereof dissolved in the aqueous phase. The N-(phosphonomethyl)glycine is present in a concentration that is biologically effective when the composition is diluted in a suitable volume of water and applied to the foliage of a susceptible plant. The oil phase of the composition comprises a carfentrazone-ethyl herbicide dissolved therein in a concentration that is biologically effective when the composition is diluted in a suitable volume of water and applied to the foliage of a susceptible plant. The composition of the invention further comprises at least one emulsifying agent having a tertiary amine functionality present in a concentration sufficient to provide acceptable physical stability of the microemulsion.

The present invention is further directed to a liquid concentrate herbicidal microemulsion composition comprising a continuous aqueous phase comprising N-(phosphonomethyl)glycine or a salt thereof. The N-(phosphonomethyl)glycine is present in a concentration that is biologically effective when the composition is diluted in a suitable volume of water and applied to the foliage of a susceptible plant. The composition further comprises a discontinuous oil phase comprising carfentrazone-ethyl in a substantially water-immiscible organic solvent, wherein the carfentrazone-ethyl is present in a concentration that is biologically effective when the composition is diluted in a suitable volume of water and applied to the foliage of a susceptible plant. Still further, the composition additionally comprises a stabilizing agent present in a concentration sufficient to inhibit substantial degradation of the carfentrazone-ethyl; one or more emulsifying agents having a tertiary amine functionality present in a concentration sufficient to provide acceptable physical stability of the microemulsion; and, one or more dispersing agents present in a concentration sufficient to provide acceptable dispersion of the microemulsion upon dilution thereof in a suitable volume of water for application to plants, but not sufficient to destabilize the microemulsion prior to such dilution.

Still further, the present invention is directed to an emulsion composition having a continuous aqueous phase and a discontinuous oil phase. The composition comprises N-(phosphonomethyl)glycine or a salt thereof in the aqueous phase and carfentrazone-ethyl in the oil phase. The N-(phosphonomethyl)glycine and the carfentrazone-ethyl are independently present in a concentration that is biologically effective when the composition is diluted in a suitable volume of water and applied to the foliage of a susceptible plant. The composition further comprises a substantially water-immiscible organic solvent in the oil phase, a water-soluble halide salt or hydrochloric acid present in a concentration sufficient to inhibit substantial degradation of the carfentrazone-ethyl and one or more surfactants present in a concentration sufficient to provide acceptable physical stability of the emulsion and provide acceptable dispersion of the emulsion upon dilution thereof in a suitable volume of water for application to plants.

Still further, the present invention is directed to an emulsion composition having a continuous aqueous phase and a discontinuous oil phase. The composition comprises N-(phosphonomethyl)glycine or a salt thereof in the aqueous phase and carfentrazone-ethyl in the oil phase. The N-(phosphonomethyl)glycine and the carfentrazone-ethyl are both independently present in a concentration that is biologically effective when the composition is diluted in a suitable volume of water and applied to the foliage of a susceptible plant. The composition further comprises a substantially water-immiscible organic solvent in the oil phase, wherein the organic solvent is selected such that the carfentrazone-ethyl has an organic solvent/water partition coefficient, expressed as a logarithm, of about 4 or greater; a water-soluble halide salt or hydrochloric acid present in a concentration sufficient to inhibit substantial degradation of the carfentrazone-ethyl; and one or more surfactants present in a concentration sufficient to provide acceptable physical stability of the emulsion, and provide acceptable dispersion of the emulsion upon dilution thereof in a suitable volume of water for application to plants.

Still further, the present invention is directed to compositions as described above that have a viscosity of not greater than about 1000 cPs at 10° C., that have a cloud point not lower than about 50° C. and that exhibit substantially no crystallization or phase separation when stored at a temperature of from about 10° to about 30° C. for a period of about 30 days. Further, the above compositions provide for high loading of water-soluble herbicides. For example, herbicidal effective concentrations of the water-soluble herbicide N-(phosphonomethyl)glycine can be as high as 360 to 500 g a.e./l in the stable compositions of the invention.

Description of the Preferred Embodiments

In accordance with the present invention, stable coformulations of an oil-soluble herbicide and a water-soluble herbicide have been discovered. In one embodiment, a liquid composition of the invention comprises an oil-in-water microemulsion having a continuous aqueous phase and a discontinuous oil phase. The water-soluble herbicide is present in solution in the continuous aqueous phase of the microemulsion, and the oil-soluble herbicide is present in solution in the discontinuous oil phase of the microemulsion. Compositions of the present invention provide for an increased weed control spectrum, more rapid burndown, early symptomology and are relatively easy to use.

It is important to note that although the description of the preferred embodiments are directed to stable microemulsions of the present invention, the principles disclosed herein are equally applicable to the preparation of stable oil-in-water emulsions, water-in-oil emulsions, macroemulsions, suspensions or suspoemulsions wherein at least two herbicidal active ingredients, one of which is a water-soluble herbicide and the other of which is an oil-soluble herbicide, are coformulated in a stable herbicidal composition. Thus, liquid concentrate compositions of the present invention can be oil-in-water macroemulsions or microemulsions, water-in-oil emulsions or water-in-oil-in-water multiple emulsions. Further, all types of concentrate formulations having characteristics of an emulsion, including suspoemulsions, are possible within the invention.

Preferably, the composition is a herbicidal concentrate, i.e., it is normally diluted in a suitable volume of water before application, for example, by spraying onto the foliage of plants. Typically, a concentrate composition contains at least about 5% by weight and up to about 50% by weight of herbicidal active ingredients. Stated another way, the combined concentration of the water-soluble herbicide and the oil-soluble herbicide comprises at least about 5% and up to about 50% by weight of the composition. Preferably, the combined concentration of the water-soluble herbicide and the oil-soluble herbicide comprises at least about 10% by weight of the composition, more preferably at least about 20% by weight.

Compositions of the invention have a viscosity of not greater than about 1000 cPs at 10° C., more preferably, a viscosity of not greater than about 500 cPs at 10° C., even more preferably not greater than about 250 cPs at 10° C. Further, compositions of the invention have a cloud point not lower than about 50° C. and preferably exhibit substantially no crystallization or phase separation when stored at a temperature of from about 10° to about 30° C. for a period of about 30 days. More preferably, a composition of the invention shows substantially no crystallization or phase separation for a period of at least about 180 days when stored at a temperature of about 10° to about 30° C. More preferably, substantially no crystallization or phase change occurs in a composition of the invention when stored for a period of at least about 30 days, most preferably for a period of at least about 180 days, at storage temperatures of from about −10° to about 40° C.

The aqueous phase of a composition of the invention comprises water having the selected water-soluble herbicide dissolved therein. The term "water-soluble" as used herein in relation to a herbicide or salt thereof means having a solubility in deionized water at 20° C. of not less than about 50 g/l. Preferred water-soluble herbicides have a solubility in deionized water at 20° C. of not less than about 200 g/l. Particularly preferred water-soluble herbicides have a herbicidal active acid or anionic moiety and are most usefully present in a composition of the invention in the form of one or more water-soluble salts. The aqueous phase can optionally contain, in addition to the water-soluble herbicide, other salts contributing to the ionic strength of the aqueous phase.

A particularly preferred group of water-soluble herbicides are those that are normally applied post-emergence to the foliage of plants. While the invention is not limited to any particular class of foliar-applied water-soluble herbicide, it has been found to provide useful benefits for compounds that rely at least in part for their herbicidal effectiveness on systemic movement in plants. Systemic movement in plants can take place via apoplastic (non-living) pathways, including within xylem vessels and in intercellular spaces and cell walls, via symplastic (living) pathways, including within phloem elements and other tissues composed of cells connected symplastically by plasmodesmata, or via both apoplastic and symplastic pathways. For foliar-applied systemic herbicides, the most important pathway is the phloem, and the present invention is believed to provide the greatest benefits where the water-soluble herbicide is phloem-mobile. However, compositions of the invention can also be useful where the water-soluble herbicide is non-systemic, as in the case of paraquat.

Water-soluble herbicides suitable for use in compositions of the invention include acifluorfen, acrolein, amitrole, asulam, benazolin, bentazon, bialaphos, bromacil, bromoxynil, chloramben, chloroacetic acid, clopyralid, 2,4-D, 2,4-DB, dalapon, dicamba, dichlorprop, difenzoquat, diquat, endothall, fenac, fenoxaprop, flamprop, flumiclorac, fluoroglycofen, flupropanate, fomesafen, fosamine, glufosinate, glyphosate, imazameth, imazamethabenz, imazamox, imazapic, imazapyr, imazaquin, imazethapyr, ioxynil, MCPA, MCPB, mecoprop, methylarsonic acid, naptalam, nonanoic acid, paraquat, picloram, quinclorac, sulfamic acid, 2,3,6-TBA, TCA, triclopyr and water-soluble salts thereof.

Phloem-mobile herbicides that are preferred for use in compositions of the invention include but are not limited to aminotriazole, asulam, bialaphos, clopyralid, dicamba, glufosinate, glyphosate, imidazolinones such as imazameth, imazamethabenz, imazamox, imazapic, imazapyr, imazaquin and imazethapyr, phenoxies such as 2,4-D, 2,4-DB, dichlorprop, MCPA, MCPB and mecoprop, picloram and triclopyr. A particularly preferred group of water-soluble herbicides are salts of bialaphos, glufosinate and glyphosate. Another particularly preferred group of water-soluble herbicides are salts of imidazolinone herbicides.

Compositions of the invention can optionally contain more than one water-soluble herbicide in solution in the aqueous phase.

An especially preferred water-soluble herbicide useful in a composition of the present invention is glyphosate, the acid form of which is alternatively known as N-(phosphonomethyl)glycine. For example, glyphosate salts useful in compositions of the present invention are disclosed in U.S. Pat. Nos. 3,799,758 and No. 4,405,531. Glyphosate salts that can be used according to the present invention include but are not restricted to alkali metal salts, for example sodium and potassium salts; ammonium salts; $C_{1-6}$ alkylammonium salts, for example dimethylammonium and isopropylammonium salts; $C_{1-6}$ alkanolammonium salts, for example monoethanolammonium salts; $C_{1-6}$ alkylsulfonium salts, for example trimethylsulfonium salts; and mixtures thereof. The N-phosphonomethylglycine molecule has three acid sites having different pKa values. Accordingly mono-, di- and tribasic salts, or any mixture thereof, or salts of any intermediate level of neutralization, can be used.

The oil phase of a composition of the present invention comprises a solvent having an oil-soluble herbicidal active ingredient dissolved therein. Oil-soluble herbicides suitable for use in compositions of the present invention include but are not limited to acetochlor, aclonifen, alachlor, ametryn, amidosulfuron, anilofos, atrazine, azafenidin, azimsulfuron, benfluralin, benfuresate, bensulfuron-methyl, bensulide, benzfendizone, benzofenap, bifenox, bromobutide, bromofenoxim, butachlor, butafenacil, butamifos, butralin, butroxydim, butylate, cafenstrole, carfentrazone-ethyl, carbetamide, chlomethoxyfen, chlorbromuron, chloridazon, chlorimuron-ethyl, chlorotoluron, chlornitrofen, chlorotoluron, chlorpropham, chlorsulfuron, chlorthal-dimethyl, chlorthiamid, cinidon-ethyl, cinmethylin, cinosulfuron, clethodim, clodinafop-propargyl, clomazone, clomeprop, cloransulam-methyl, cyanazine, cycloate, cyclosulfamuron, cycloxydim, cyhalofop-butyl, daimuron, desmedipham, desmetryn, dichlobenil, diclofop-methyl, diflufenican, dimefuron, dimepiperate, dimethachlor, dimethametryn, dimethenamid, dinitramine, dinoterb, diphenamid, dithiopyr, diuron, EPTC, esprocarb, ethalfluralin, ethametsulfuron-methyl, ethofumesate, ethoxysulfuron, etobenzanid, fenoxaprop-ethyl, fenuron, flamprop-methyl, flazasulfuron, fluazifop-butyl, fluazifop-P-butyl, fluazolate, fluchloralin, flumetsulam, flumiclorac-pentyl, flumioxazin, fluometuron, fluorochloridone, fluoroglycofen-ethyl, flupoxam, flurenol, fluridone, fluroxypyr-1-methylheptyl, flurtamone, fluthiacet-methyl, fomesafen, graminicides, halosafen, halosulfuron, haloxyfop, hexazinone, imazosulfuron, indanofan, isoproturon, isouron, isoxaben, isoxaflutole, isoxapyrifop, lactofen, lenacil, linuron, mefenacet, metamitron, metazachlor, methabenzthiazuron, methyldymron, metobenzuron, metobromuron, metolachlor, metosulam, metoxuron, metribuzin, metsulfuron, molinate, monolinuron, naproanilide, napropamide, neburon, nicosulfuron, norflurazon, orbencarb, oryzalin, oxadiargyl, oxadiazon, oxasulfuron, oxyfluorfen, pebulate, pendimethalin, pentanochlor, pentoxazone, phenmedipham, piperophos, pretilachlor, primisulfuron, prodiamine, profluazol, prometon, prometryn, propachlor, propanil, propaquizafop, propazine, propham, propisochlor, propyzamide, prosulfocarb, prosulfuron, pyraflufen-ethyl, pyrazogyl, pyrazolynate, pyrazosulfuron-ethyl, pyrazoxyfen, pyributicarb, pyridate, pyriminobac-methyl, quinclorac, quinmerac, quizalofop, quizalofop-P, rimsulfuron, sethoxydim, siduron, simazine, simetryn, sulcotrione, sulfentrazone, sulfometuron, sulfosulfuron, tebutam, tebuthiuron, tepraloxydim, terbacil, terbumeton, terbuthylazine, terbutryn, thenylchlor, thiazopyr, thidiazimin, thifensulfuron, thiobencarb, tiocarbazil, tralkoxydim, triallate, triasulfuron, tribenuron, trietazine, trifluralin, triflusulfuron and vernolate.

Preferred oil-soluble herbicides for use in a composition of the invention include but are not limited to acetochlor, aclonifen, alachlor, ametryn, amidosulfuron, anilofos, atrazine, azafenidin, azimsulfuron, benfluralin, benfuresate, bensulfuron-methyl, bensulide, benzfendizone, benzofenap, bromobutide, bromofenoxim, butachlor, butafenacil, butamifos, butralin, butroxydim, butylate, cafenstrole, carfentrazone-ethyl, carbetamide, chlorbromuron, chloridazon, chlorimuron-ethyl, chlorotoluron, chlornitrofen, chlorotoluron, chlorpropham, chlorsulfuron, chlorthal-dimethyl, chlorthiamid, cinidon-ethyl, cinmethylin, cinosulfuron, clethodim, clodinafop-propargyl, clomazone, clomeprop, cloransulam-methyl, cyanazine, cycloate, cyclosulfamuron, cycloxydim, cyhalofop-butyl, daimuron, desmedipham, desmetryn, dichlobenil, diclofop-methyl, diflufenican, dimefuron, dimepiperate, dimethachlor, dimethametryn, dimethenamid, dinitramine, dinoterb, diphenamid, dithiopyr, diuron, EPTC, esprocarb, ethalfluralin, ethametsulfuron-methyl, ethofumesate, ethoxysulfuron, etobenzanid, fenoxaprop-ethyl, fenuron, flamprop-methyl, flazasulfuron, fluazifop-butyl, fluazifop-P-butyl, fluazolate, fluchloralin, flumetsulam, flumiclorac-pentyl, flumioxazin, fluometuron, fluorochloridone, flupoxam, flurenol, fluridone, fluroxypyr-1-methylheptyl, flurtamone, fluthiacet-methyl, graminicides, halosulfuron, haloxyfop, hexazinone, imazosulfuron, indanofan, isoproturon, isouron, isoxaben, isoxaflutole, isoxapyrifop, lenacil, linuron, mefenacet, metamitron, metazachlor, methabenzthiazuron, methyldymron, metobenzuron, metobromuron, metolachlor, metosulam, metoxuron, metribuzin, metsulfuron, molinate, monolinuron, naproanilide, napropamide, neburon, nicosulfuron, norflurazon, orbencarb, oryzalin, oxadiargyl, oxadiazon, oxasulfuron, pebulate, pendimethalin, pentanochlor, pentoxazone, phenmedipham, piperophos, pretilachlor, primisulfuron, prodiamine, profluazol, prometon, prometryn, propachlor, propanil, propaquizafop, propazine, propham, propisochlor, propyzamide, prosulfocarb, prosulfuron, pyraflufen-ethyl, pyrazogyl, pyrazolynate, pyrazosulfuron-ethyl, pyrazoxyfen, pyributicarb, pyridate, pyriminobac-methyl, quinclorac, quinmerac, quizalofop, quizalofop-P, rimsulfuron, sethoxydim, siduron, simazine, simetryn, sulcotrione, sulfentrazone, sulfometuron, sulfosulfuron, tebutam, tebuthiuron, tepraloxydim, terbacil, terbumeton, terbuthylazine, terbutryn, thenylchlor, thiazopyr, thidiazimin, thifensulfuron, thiobencarb, tiocarbazil, tralkoxydim, triallate, triasulfuron, tribenuron, trietazine, trifluralin, triflusulfuron and vernolate.

Another class of preferred oil-soluble herbicides for use in a composition of the invention are protoporyphinogen oxidase inhibitor (PPO) herbicides. PPO herbicides are known to affect plants by inhibiting protoporphyrinogen oxidase in chloroplasts, thereby disrupting photosynthesis and other biological processes and causing early symptoms of tissue necrosis in plants. General classes of PPO herbicides include diphenylether herbicides (e.g., bifenox, chlomethoxyfen, fluoroglycofen-ethyl, fomesafen, halosafen, lactofen and oxyfluorfen); phenylpyrazoles (e.g., fluazolate and pyraflufen-ethyl); N-phenylphthalimides (e.g., cinidon-ethyl, flumioxazin and flumiclorac-pentyl); thiadiazoles (e.g., fluthiacet-methyl and thidiazimin); oxadiazoles (e.g., oxadiazon and oxadiargyl); triazolinones (e.g., azafenidin, carfentrazone-ethyl and sulfentrazone); oxazolidinediones (e.g., pentoxazone); pyrimidindiones (e.g., benzfendizone and butafencil); pyrazogyl and profluazol.

A particularly preferred class of PPO herbicides are the triazolinones. Triazolinone herbicides are known to provide good control of broadleaf weeds but are less efficacious in controlling grasses. Suitable triazolinone herbicides for use in compositions of the invention are described generally in U.S. Pat. Nos. 5,217,520 and 5,125,958 to Poss and U.S. Pat. No. 4,818,275 to Theodoridis, all of which are hereby incorporated herein by reference. A triazolinone herbicide suitable for use in a composition of the invention can be a compound of the structure shown in the following formula:

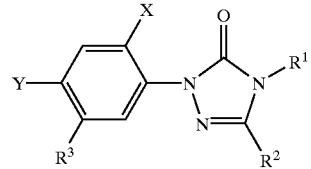

or a tautomer thereof, wherein $R^1$ is haloalkyl; $R^2$ is halogen or lower alkyl; $R^3$ is —$CH_2CHClCO_2R^4$ or —$NHSO_2R^5$; $R^4$ is alkyl, alkoxycarbonylalkyl, cycloalkyl, benzyl, chlorobenzyl, alkylbenzyl, or haloalkylbenzyl; $R^5$ is alkyl, haloalkyl, dialkylamino, carboxymethyl, hydroxy, or aryl; X is hydrogen, halogen, alkyl, alkoxy, haloalkyl, or nitro; and Y is hydrogen, halogen, alkyl, alkoxy, haloalkyl, haloloweralkylsulfinyl, or haloloweralkoxy.

In a preferred composition, $R^1$ is difluoromethyl and $R^2$ is lower alkyl, more preferably $C_1$ to about $C_5$ alkyl, and still more preferably methyl. $R^4$ is preferably alkyl or alkoxy, more preferably alkyl, still more preferably $C_1$ to about $C_5$ alkyl, and most preferably ethyl. $R^5$ is preferably alkyl, more preferably $C_1$ to about $C_5$ alkyl, and most preferably methyl. X is preferably a halogen and more preferably X is fluoro or chloro. Y is preferably a halogen, more preferably chloro. When $R^3$ is —$CH_2CHClCO_2R^4$, the triazolinone herbicide is a triazolinone acid ester herbicide. A particularly preferred triazolinone herbicide is carfentrazone-ethyl having a structure as follows:

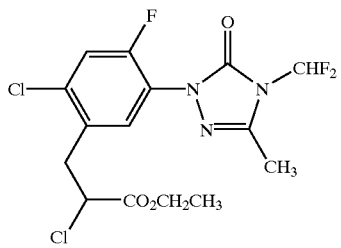

When $R^3$ is —$NHSO_2R^5$, the triazolinone herbicide is a triazolinone sulfonamide herbicide. Another particularly preferred triazolinone herbicide is sulfentrazone having the following structure:

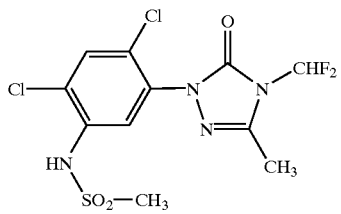

In a composition of the invention, the herbicidal active ingredients are generally present in an amount which is biologically effective when the composition is diluted in a suitable volume of water and applied to the foliage of a susceptible plant. Typically, the oil-soluble herbicide is present in a concentration such that the weight ratio of water-soluble herbicide to oil-soluble herbicide ranges from about 190:1 to about 1:1. For example, when the oil-soluble herbicide is a PPO herbicide such as a triazolinone, the weight ratio of triazolinone to water-soluble herbicide ranges from about 190:1 to about 19:1. In any case, the concentration of the oil-soluble herbicide in the composition as a whole is about 0.1% to about 25% by weight. In preferred compositions, the concentration of the oil-soluble herbicide is about 0.1% to about 5% by weight, for example about 0.2% to about 2% by weight.

A key to the present invention is to select as the solvent for the oil-soluble herbicide, i.e., as the basis for the oil phase, an organic liquid having the following properties. First, the solvent must be substantially immiscible with water. Second, the affinity of the solvent for the oil-soluble herbicide in question must be such that substantially all of the oil-soluble herbicide is partitioned in the oil phase and substantially none is partitioned in the aqueous phase. One skilled in the art will readily be able to determine whether a particular organic solvent meets this second criterion for the oil-soluble herbicide in question by following any standard test procedure for determining partition of a compound (in this case, the oil-soluble herbicide) between water and the organic solvent.

For example, one such test procedure comprises the following steps.

1. A solution of the oil-soluble herbicide is prepared in the organic solvent at as high a concentration as possible up to 15% by weight.
2. An aliquot of 10 g of this solution is added to 90 g water in a glass bottle, which is shaken on a mechanical shaker for 4 hours at ambient temperature.
3. The contents of the glass bottle are permitted to phase separate for 4 days.
4. Subsamples of the resulting oil and water phases are taken and analyzed by HPLC to determine concentrations $C_O$ and $C_W$ in the oil and water phases respectively. The subsample of the water phase is preferably centrifuged before analysis to remove traces of organic solvent.
5. A partition coefficient, analogous to octanol-water partition coefficient P, is calculated as $C_O/C_W$. The partition coefficient is conveniently expressed as a logarithm.

In many cases the concentration of the oil-soluble herbicide in the water phase will be below the detection limit of the HPLC method. In other cases, traces of the organic solvent are found in the water phase, even after centrifugation, so that the apparent concentration of oil-soluble herbicide observed in the water phase is misleadingly high. In such cases, a published value for solubility in water of the oil-soluble herbicide in question can be used in place of $C_W$ for calculation of the partition coefficient.

The organic solvent is selected such that the oil-soluble herbicide exhibits a partition coefficient such that log $(C_O C_W)$ is about 4 or greater, preferably about 5 or greater. Preferably the oil-soluble herbicide is soluble in the organic solvent by at least about 5% by weight, more preferably by at least about 10% by weight and most preferably by at least about 15% by weight. Generally, organic solvents having a higher solubility of the oil-soluble herbicide therein are more suitable, provided the organic solvent is substantially immiscible with water.

Organic solvents useful in compositions of the present invention preferably have a flash point above about 35° C., more preferably above about 90° C., and are preferably not antagonistic to the herbicidal effectiveness of any of the herbicidal active ingredients of the composition. Examples of suitable solvents for use in the present invention include naphthalenic aromatic solvents such as Aromatic 100, Aromatic 150 or Aromatic 200, commercially available from Exxon Mobil Chemical of Houston, Tex. or Sure Sol 225, commercially available from Koch Specialty Chemical Co. of Houston, Tex.; and alkyl acetates with high solvency, such as Exxate™ 1000, also available from Exxon Mobil Chemical. In particular, when the water-soluble herbicide is a salt of glyphosate, an aromatic solvent is especially preferred. Useful aromatic solvents include benzene, toluene, o-xylene, m-xylene, p-xylene, mesitylene, naphthalene, bis-(α-methylbenzyl)xylene, phenylxylene and combinations thereof. Other useful solvents include substituted aromatic solvents such as chlorobenzene or ortho-dichlorobenzene.

The amount of the selected organic solvent to be used is important. Clearly the amount must be sufficient to completely dissolve the oil-soluble herbicide. Even for an organic solvent in which the oil-soluble herbicide is highly soluble, the weight ratio of organic solvent to oil-soluble herbicide should not be less than about 3:1. If too small an amount of organic solvent is used, protection of the oil-soluble herbicide from water can be compromised, leading to increased rates of chemical degradation. The weight ratio of organic solvent to oil-soluble herbicide can be much higher than 3:1, but economics and environmental considerations typically militate against excessively high amounts of organic solvent. Thus, an upper limit of the weight ratio for practical purposes is about 75:1. In preferred compositions of the invention, the weight ratio of organic solvent to oil-soluble herbicide is about 3:1 to about 60:1, more preferably about 5:1 to about 50:1.

A composition of the invention further comprises one or more surfactants. As indicated above, these surfactants can function as emulsifying agents, dispersing agents and/or adjuvants for enhancing herbicidal efficacy. However, the presence of surfactants can be detrimental to the stability of a microemulsion as surfactants can facilitate contact of the oil-soluble herbicide with water, thereby promoting chemical degradation of the oil-soluble herbicide. The compositions of the invention contain one or more surfactants present in a concentration sufficient to provide acceptable physical stability of the composition, and provide acceptable dispersion of the composition upon dilution thereof in a suitable volume of water for application to plants. Therefore, as an important feature of the present invention, it has been discovered that, when one or more emulsifying agents and one or more dispersing agents are selected in accordance with the invention, chemical degradation can be kept to an acceptable minimum by including less than about 10% by weight of the emulsifying agent(s) and less than about 5% of the dispersing agent(s) in the composition. Preferably the amount of all surfactants in the composition is less than about 12% by weight, and more preferably from about 4% to less than about 12%. Ideally, the amount of surfactants included is not substantially more than the minimum needed for acceptable physical stability and acceptable dispersibility in water. Minimum levels of emulsifying and dispersing agents can readily be determined by one skilled in the art as indicated above.

A composition of the invention includes at least one surfactant which is an emulsifying agent. The emulsifying agent preferably has a tertiary amine functionality. Preferred tertiary amine surfactants have a hydrophobic moiety comprising a linear or branched saturated or unsaturated aliphatic hydrocarbyl group having about 8 to about 22 carbon atoms, this moiety being referred to herein as an "alkyl" group consistent with conventional use of the term "alkyl" in surfactant-related literature. Such tertiary amine surfactants typically also enhance the herbicidal effectiveness of the composition by various means, including assisting adherence to, and thereby retention on, plant foliage of the spray composition obtained by diluting the composition in water, and facilitating penetration of the active ingredients through cuticles on the surface of plant foliage. This is especially true where the water-soluble herbicide is a salt of glyphosate.

Quaternary ammonium surfactants can also be effective emulsifiers and provide good herbicidal efficacy enhancement; however, quaternary ammonium surfactants are not preferred in compositions of the invention because, at least when present in large amounts, they promote increased rates of chemical degradation of the oil-soluble herbicide. Without being bound to a particular theory, it is believed that the increased chemical degradation associated with the presence of quaternary ammonium surfactants results from their effectiveness in facilitating transfer of the oil-soluble herbicide from the oil phase to the aqueous phase. Highly water-soluble quaternary ammonium surfactants such as benzalkonium chloride (a mixture of alkyl dimethyl benzyl ammonium chlorides) are less troublesome in this regard than quaternary ammonium surfactants that are other than water-soluble, such as polyoxyethylene (2) N-methyl alkylammonium chlorides (N,N-bis(hydroxyethyl) -methyl alkylammonium chlorides). Compositions of the invention preferably contain no substantial amount of quaternary ammonium surfactants that are water-insoluble.

Tertiary amine surfactants for use as the emulsifying agent(s) are preferably selected from polyoxyethylene (2–20) tertiary alkylamines and polyoxyethylene (2–20) tertiary alkyletheramines. In particularly preferred compositions of the invention, the alkyl chains of these surfactants have about 12 to about 18 carbon atoms. Often the alkyl chains are derived from natural oils or fats such as coconut oil, soybean oil or beef tallow, and the resulting surfactants therefore typically contain a variety of alkyl chain lengths and degrees of unsaturation. Preferred tertiary alkylamines for use in the present invention include polyoxyethylene (2–10) cocoamine and polyoxyethylene (2–10) tallowamine, which are commercially available from many surfactant suppliers. For example, Ethomeen™ C15 (polyoxyethylene (5) cocoamine) and Ethomeen™ T15 (polyoxyethylene (5) tallowamine) are two of such tertiary alkylamines commercially available from Akso Nobel Surface Chemistry LLC of Chicago, Ill. Suitable polyoxyethylene alkyletheramines for use in compositions of the invention are disclosed in U.S. Pat. No. 5,750,468 to Wright et al. In preferred compositions of the invention, it will often be found desirable to include at least two tertiary amine surfactants, one being more hydrophilic than the other, for example polyoxyethylene (5) tallowamine and polyoxyethylene (2) cocoamine respectively.

The minimum amount of emulsifying agent(s) required to provide acceptable physical stability depends, among other things, on the amount of organic solvent present, which depends in turn on the amount of oil-soluble herbicide present. Typically, the amount of emulsifying agent(s) in compositions of the invention ranges from about 3% to about 10% by weight, more preferably about 3% to about 8% by weight, and even more preferably about 3% to about 6% by weight.

For some oil-soluble herbicides, it has been found that quaternary alkylammonium chloride surfactants are more effective emulsifying agents than the corresponding tertiary alkylamines. For example, polyoxyethylene (2–5) N-methyl alkylammonium chlorides are very effective emulsifiers. However, as indicated above, these quaternary ammonium surfactants are unacceptable at relatively high concentration because they promote chemical degradation of the oil-soluble herbicide. Yet, when tertiary amines alone are used, acceptable physical stability is not always achievable.

A solution to this problem lies in the surprising discovery that inclusion of a stabilizing agent, such as a water-soluble chloride surfactant, substantially dispersed in and associated with the aqueous phase can provide enhanced physical stability when tertiary amine surfactants are used as emulsifiers. In particular, water-soluble quaternary ammonium chloride surfactants such as benzalkonium chloride are preferred. Without being held to a particular theory, it has been found that such water-soluble quaternary ammonium chloride surfactants have a lesser tendency to promote chemical degradation of the oil-soluble herbicide than other, less water-soluble quaternary ammonium chlorides such as polyoxyethylene (2–5) N-methyl alkylammonium chlorides and thus, are acceptable ingredients in compositions of the invention. However, it is nonetheless preferred that the amount of the stabilizing agent does not exceed about 6% by weight of the composition. A minimum effective stabilizing amount of a stabilizing agent can be determined by routine evaluation of physical stability in any particular situation. Preferred amounts of such a stabilizing agent, for example benzalkonium chloride, are about 1% to about 6%, more preferably about 1% to about 4%, by weight of the composition.

Even more surprisingly, it has been found that physical stability can be enhanced by including a non-surfactant stabilizing agent that is substantially dispersed in and associated with the aqueous phase of compositions of the invention. For example, low molecular weight ($C_{1-6}$) organic ammonium halides, preferably ($C_{1-6}$) organic ammonium chlorides such as isopropylammonium chloride, can be used, as can ammonium chloride. Alkali metal halides, preferably alkali metal chlorides such as sodium chloride or potassium chloride are also effective, as is hydrochloric acid. Where the water-soluble herbicide is a salt of glyphosate, preferred water-soluble chlorides are ammonium chloride, sodium chloride and hydrochloric acid. Hydrochloric acid can be especially useful where a downward adjustment of the pH of the aqueous phase is desired. An effective stabilizing amount of a water-soluble chloride in any particular situation can be determined by routine evaluation of physical stability as indicated previously. Where used, preferred amounts of low molecular weight organic ammonium chlorides, ammonium chloride, alkali metal chlorides and/or hydrochloric acid are those providing about 0.5% to about 2.5% chloride ion by weight of the composition.

Compositions of the invention may further contain one or more dispersing agents. Generally, any nonionic surfactant known to be effective as a dispersing agent for liquid concentrate herbicidal formulations can be used as a dispersing agent in a composition of the invention. However, the dispersing agent is preferably one or more surfactants selected from polyoxyethylene (2–20) alkylethers and alkylphenylethers, the term "alkyl" having the same meaning as in the context of the tertiary amine surfactants described above. Preferably, the amount of dispersing agents in a composition of the invention range from about 0.5% to about 5% by weight, and more preferably from about 0.5% to about 3% by weight, of the composition.

As used herein, it is to be noted that an amount of the selected emulsifying agent(s) "sufficient to provide acceptable physical stability of the composition" can be readily determined by one of skill in the art by routine evaluation of a range of compositions having differing amounts of the emulsifying agent(s). Typically, physical stability of the composition is acceptable if no significant phase separation is evident following storage for at least 7 days at any temperature in the range from about 0° C. to about 40° C. Where the composition is one that additionally requires the presence of a water-soluble chloride for acceptable physical stability, routine evaluation of differing amounts of the emulsifying agent(s) is conducted in the presence of such water-soluble chloride.

Further, a "stabilizing" amount of one or more selected water-soluble chlorides as used above is an amount that provides acceptable physical stability of the compositions as defined above, when present along with an emulsifying agent(s) in an amount insufficient on its own to provide such stability. One of skill in the art can readily determine such a stabilizing amount by routine evaluation of a range of compositions having differing amounts of the selected chloride(s).

It is to be further noted that, as used above, an amount of the selected dispersing agent(s) "sufficient to provide acceptable dispersion of the composition upon dilution thereof in a suitable volume of water for application to plants" can readily be determined by one of skill in the art by routine evaluation of a range of compositions having differing amounts of the selected dispersing agent(s). A suitable volume of water is that which upon dilution of the composition provides an application treatment composition having a concentration of active ingredients adequate to kill or control susceptible plants if applied to foliage of such plants. Dispersion of the composition in such a volume of water is acceptable if no visible aggregation or flocculation of water-insoluble ingredients is observed. Therefore, an amount of the selected dispersing agent(s) "not sufficient to destabilize the composition" is an amount lower than that which results in the composition losing the acceptable physical stability it has in the absence of the dispersing agent(s). Such an amount can readily be determined by one of skill in the art by routine evaluation of a range of compositions having differing amounts of the selected dispersing agent(s).

Compositions of the invention can optionally contain additional desired agriculturally acceptable ingredients, including surfactants of classes other than those defined above. Standard reference sources from which one of skill in the art can select suitable surfactants, without limitation to the above mentioned classes, include Handbook *of Industrial Surfactants,* Second Edition (1997) published by Gower, *McCutcheon's Emulsifiers and Detergents,* North American and International Editions (1997) published by MC Publishing Company, and *International Cosmetic Ingredient Dictionary,* Sixth Edition (1995) Volumes 1 and 2, published by the Cosmetic, Toiletry and Fragrance Association.

Other optional components of compositions of the invention include agents to modify color, viscosity, gelling properties, freezing point, hygroscopicity, caking behavior, dissolution rate, dispersibility, or other formulation characteristics.

In a particularly preferred embodiment of the invention, the pH of the aqueous phase of the composition is in a range that is minimally conducive to chemical degradation of the oil-soluble herbicide. The water-soluble herbicide can, in some cases, naturally provide a pH in the desired range; in other cases an acid, e.g., hydrochloric acid, or base, e.g., potassium hydroxide or isopropylamine, can be added to adjust the pH. The effect of pH on degradation of the particular oil-soluble herbicide of choice can be determined by empirical testing, but is often known and available in standard reference sources such as *The Pesticide Manual,* 11th Edition (1997), published by the British Crop Protection Council.

When an organic solvent is selected for the oil-soluble herbicide in accordance with the present invention, partition of the oil-soluble herbicide is so overwhelmingly in the oil phase that mean residence time in the aqueous phase of individual molecules of the oil-soluble herbicide is extremely short, and the opportunity for chemical degradation of the oil-soluble herbicide is accordingly very small. However, the adjustment of pH as just described is desirable to further reduce the potential for chemical degradation and permit the longest possible shelf-life for the composition.

A process of preparing a composition of the invention comprises mixing the various ingredients in a suitable vessel. It is important to note that mixing is not critical to the invention and any order of addition of ingredients is suitable. However, experience to date suggests that certain orders of addition in preparing compositions of the invention require less reaction time. Therefore, a presently preferred order of addition of the ingredients involves adding all required surfactants to a concentrated aqueous solution of the water-soluble herbicide along with an acid or base for pH adjustment, if desired, to form a first mixture. The oil-soluble herbicide is added to the organic solvent with agitation to form a second mixture. The second mixture is then added to the first mixture with agitation to form the finished composition.

An alternative order of addition involves mixing a concentrated aqueous solution of the water-soluble herbicide together with other, optional, water-soluble ingredients including an acid or base for pH adjustment, with agitation to form a first mixture. The oil-soluble herbicide is then added to the organic solvent with agitation to form a second mixture. The second mixture is added to the first mixture with agitation, then the surfactants are added. Agitation is continued until a physically stable composition is formed.

In a particularly preferred composition of the invention, the oil-soluble herbicide is carfentrazone-ethyl, a PPO herbicide of the triazolinone class, and the water-soluble herbicide is a salt of N-(phosphonomethyl)glycine ("glyphosate").

Carfentrazone-ethyl, as described in U.S. Pat. No. 5,217,520 incorporated herein by reference, and otherwise known as ethyl α,2-dichloro-5-(4-(difluoromethyl)-4,5-dihydro-3-methyl-5-oxo-1H-1,2,4-triazol-1-yl)-4-fluorobenzenepropionate, CAS Registry Number 128639-02-1, is a high-melting solid carboxylic acid useful for post-emergent control primarily of broadleaf weeds known for its rapid uptake and early symptomology. N-(phosphonomethyl)glycine, on the other hand, is a widely-used broad-spectrum herbicide that does not necessarily provide early symptomology. Therefore, coformulations of carfentrazone-ethyl and N-phosphonomethyl)glycine can benefit from the broad spectrum of control of the N-(phosphonomethyl)glycine while the early symptoms caused by the carfentrazone-ethyl can serve as a marker indicating whether a given plant has been treated with the combination. Contemplated compositions of the invention comprising a salt of glyphosate and an oil-soluble triazolinone such as carfentrazone-ethyl typically contain about 50 to about 500 grams per liter of glyphosate, expressed as acid equivalent (g a.e./l). Higher glyphosate concentrations within this range, for example, about 300 to about 500 g a.e./l are preferred, even more preferably about 360 to about 500 g a.e./l.

Glyphosate (N-phosphonomethylglycine) in its strict sense is an acid compound, but the word "glyphosate" is used herein in a less restrictive sense, except where the context dictates otherwise, to encompass not only glyphosate acid but also salts, adducts and esters thereof, and compounds which are converted to glyphosate in plant tissues or which otherwise provide glyphosate ions. In most commercial formulations of glyphosate, the glyphosate is present as a water-soluble salt. In this respect, glyphosate is typical of most exogenous chemical substances that are acids or that form anions.

Herbicidal salts of glyphosate are disclosed, for example, in U.S. Pat. No. 3,799,758 to Franz, U.S. Pat. No. 3,853,530 to Franz, U.S. Pat. No. 4,140,513 to Prill, U.S. Pat. No. 4,315,765 to Large, U.S. Pat. No. 4,405,531 to Franz, U.S. Pat. No. 4,481,026 to Prisbylla and U.S. Pat. No. 4,507,250 to Bakel. In most of the salts disclosed, the counterion to glyphosate anion is a relatively low molecular weight, non-amphiphilic cation. Typical of such salts are alkali metal, for example sodium and potassium, salts; ammonium salt; and salts having an ammonium, sulfonium or sulfoxonium cation substituted with 1–3 organic groups containing in total 1–6 carbon atoms, for example dimethylammonium, isopropylammonium, ethanolammonium and trimethylsulfonium salts.

Commercial formulations of glyphosate salts include, for example, Roundup® brand, Accord® brand, Roundup® Ultra brand and Roundup® Xtra brand herbicides of Monsanto Company, which contain the isopropylammonium salt, Roundup® Dry brand and Rival® brand herbicides of Monsanto Company, which contain the ammonium salt, Roundup® Geoforce brand herbicide of Monsanto Company, which contains the sodium salt, and Touchdown® brand herbicide of Zeneca, which contains the trimethylsulfonium salt.

The selection of application rates relative to providing a desired level of herbicidal activity for a composition of the invention containing a specific water-soluble herbicide and a specific oil-soluble herbicide is within the skill of the ordinary agricultural technician. One skilled in the art will recognize that individual plant conditions, weather and growing conditions, as well as the specific exogenous chemical substance selected, can affect the results achieved in using a composition of the present invention. Where the water-soluble herbicide is a glyphosate salt, much information is available in published literature about appropriate application rates. Over two decades of glyphosate use and published studies relating to such use have provided abundant information from which a weed control practitioner can select glyphosate application rates that are herbicidally effective on particular species at particular growth stages in particular environmental conditions. Generally, preferred application rates for glyphosate are from about 100 to about 2500 g a.e./ha, more preferably from about 250 to about 1500 g a.e./ha.

The method of the present invention where the water-soluble herbicide is glyphosate, more particularly a water-soluble glyphosate salt, is applicable to any and all plant species on which glyphosate is biologically effective as a herbicide. This encompasses a very wide variety of plant species worldwide. Likewise, compositions of the invention containing a glyphosate salt can be applied to any and all plant species on which glyphosate is biologically effective. Therefore, for example, compositions of the invention containing glyphosate as an herbicidal active ingredient can be applied to a plant in a herbicidally effective amount, and can effectively control one or more plant species of one or more of the following genera without restriction: Abutilon, Amaranthus, Artemisia, Asclepias, Avena, Axonopus, Borreria, Brachiaria, Brassica, Bromus, Chenopodium, Cirsium, Commelina, Convolvulus, Cynodon, Cyperus, Digitaria, Echinochloa, Eleusine, Elymus, Equisetum, Erodium, Helianthus, Imperata, Ipomoea, Kochia, Lolium, Malva, Oryza, Ottochloa, Panicum, Paspalum, Phalaris, Phragmites, Polygonum, Portulaca, Pteridium, Pueraria, Rubus, Salsola, Setaria, Sida, Sinapis, Sorghum, Triticum, Typha, Ulex, Xanthium and Zea.

Particularly important annual broadleaf species for which glyphosate compositions are used are exemplified without limitation by the following: velvetleaf (*Abutilon theophrasti*), pigweed (Amaranthus spp.), buttonweed (Borreria spp.), oilseed rape, canola, indian mustard, etc. (Brassica spp.), commelina (Commelina spp.), filaree (Erodium spp.), sunflower (Helianthus spp.), morningglory (Ipomoea spp.), kochia (*Kochia scoparia*), mallow (Malva spp.), wild buckwheat, smartweed, etc. (Polygonum spp.), purslane (Portulaca spp.), russian thistle (Salsola spp.), sida (Sida spp.), wild mustard (*Sinapis arvensis*) and cocklebur (Xanthium spp.)

Particularly important annual narrowleaf species for which glyphosate compositions are used are exemplified without limitation by the following: wild oat (*Avena fatua*), carpetgrass (Axonopus spp.), downy brome (*Bromus tectorum*), crabgrass (Digitaria spp.), barnyardgrass (*Echinochloa crus-galli*), goosegrass (*Eleusine indica*), annual ryegrass (*Lolium multiflorum*), rice (*Oryza sativa*), ottochloa (*Ottochloa nodosa*), bahiagrass (*Paspalum notatum*), canarygrass (Phalaris spp.), foxtail (Setaria spp.), wheat (*Triticum aestivum*) and corn (*Zea mays*).

Particularly important perennial broadleaf species for which glyphosate compositions are used are exemplified without limitation by the following: mugwort (Artemisia spp.), milkweed (Asclepias spp.), canada thistle (*Cirsium arvense*), field bindweed (*Convolvulus arvensis*) and kudzu (Pueraria spp.).

Particularly important perennial narrowleaf species for which glyphosate compositions are used are exemplified without limitation by the following: brachiaria (Brachiaria spp.), bermudagrass (*Cynodon dactylon*), yellow nutsedge (*Cyperus esculentus*), purple nutsedge (*C. rotundus*), quackgrass (*Elymus repens*), lalang (*Imperata cylindrica*), perennial ryegrass (*Lolium perenne*), guineagrass (*Panicum maximum*), dallisgrass (*Paspalum dilatatum*), reed (Phragmites spp.), johnsongrass (*Sorghum halepense*) and cattail (Typha spp.).

Other particularly important perennial species for which glyphosate compositions are used are exemplified without limitation by the following: horsetail (Equisetum spp.), bracken (*Pteridium aquilinum*), blackberry (Rubus spp.) and gorse (*Ulex europaeus*).

Thus, for example, glyphosate/triazolinone compositions of the present invention, and a process for treating plants with such compositions, can be useful on any of the above species. In a particular contemplated process, a plant treatment composition is formed by diluting a composition of the invention in a suitable volume of water for application to a field. Preferably, a plant treatment composition comprising glyphosate and a triazolinone herbicide such as carfentrazone-ethyl is formed by diluting a composition of the present invention in water and the plant treatment composition is applied to weeds or undesired plants for burndown. As glyphosate is generally very effective in controlling most grass weeds, the role of the triazolinone in a glyphosate/triazolinone composition is especially to control broadleaf weeds and to act as a marker in providing rapid burndown and early visual symptoms of treatment.

Application of plant treatment compositions to foliage of plants is preferably accomplished by spraying, using any conventional means for spraying liquids, such as spray nozzles or spinning-disk atomizers. Compositions of the present invention can be used in precision farming techniques, in which apparatus is employed to vary the amount of exogenous chemical substance applied to different parts of a field, depending on variables such as the particular plant species present, plant growth stage, soil moisture status, etc. In one embodiment of such techniques, a global positioning system operated with the spraying apparatus can be used to apply the desired amount of the composition to different parts of a field.

A plant treatment composition is preferably dilute enough to be readily sprayed using standard agricultural spray equipment. Suitable application rates for the present invention vary depending upon such factors as the type and concentration of active ingredient and the plant species involved. Useful rates for applying an aqueous composition to a field of foliage can range from about 25 to about 1,000 liters per hectare (l/ha), preferably about 50 to about 300 l/ha, by spray application.

EXAMPLES

The following examples are provided for illustrative purposes only and are not intended to limit the scope of the present invention. In these examples, percentage amounts refer to percent by weight unless otherwise noted.

Examples 1 through 12 utilized Formulation L, available from Monsanto Company as MON 0139, which consists of 62% by weight of glyphosate isopropylammonium salt (IPA) in aqueous solution with no surfactant as a starting ingredient. Formulation L contains 570 g a.e./l of glyphosate.

Example 1

A microemulsion composition was prepared having the following ingredients:

| | |
|---|---|
| glyphosate IPA salt solution (MON 0139) | 67.37%[1] |
| ammonium chloride | 1.11% |
| 2N hydrochloric acid | 11.31% |
| Solvent (Aromatic 150) | 11.93% |
| carfentrazone-ethyl (91.2% active) | 0.18% |
| Emulsifier (Ethomeen T/15) | 3.07% |
| Emulsifier (Ethomeen C/15) | 2.95% |
| Dispersant (Surfonic L12-6) | 2.09% |

[1]Equivalent to 41.77% glyphosate IPA active ingredient.

Ammonium chloride (0.45 g) was dissolved in 2N hydrochloric acid (4.60 g) and the resulting solution was mixed with MON 0139 (27.41 g) to form a first mixture. Carfentrazone-ethyl (0.0739 g) was dissolved in Aromatic 150 (4.85 g) to form a second mixture, which was then added to the first mixture with agitation. Finally, surfactants Ethomeen T/15 (1.25 g), Ethomeen C/15 (1.20 g) and Surfonic L12-6 (0.85 g) were added and the whole composition was stirred, using an overhead electric stirrer, under moderate agitation for 30 minutes.

The composition was a clear amber microemulsion that was physically stable at −10° C., room temperature (approximately 22° C.) and 60° C. The microemulsion exhibited good dispersion in water.

Example 2

A microemulsion composition was prepared having the following ingredients:

| | |
|---|---|
| glyphosate IPA salt solution (MON 0139) | 67.48%[1] |
| ammonium chloride | 0.27% |
| water | 3.62% |
| 2N hydrochloric acid | 11.32% |
| Solvent (Aromatic 150) | 2.07% |
| carfentrazone-ethyl (91.2% active) | 0.18% |
| Emulsifier (Ethomeen T/15) | 3.27% |
| Emulsifier (Ethomeen C/15) | 1.26% |
| Dispersant (Surfonic L12-6) | 2.07% |

[1]Equivalent to 41.84% glyphosate IPA active ingredient.

Ammonium chloride (0.11 g) was dissolved in water (1.47 g) and 2N hydrochloric acid (4.60 g) and the resulting solution was mixed with MON 0139 (27.41 g) to form a first mixture. Carfentrazone-ethyl (0.0739 g) was dissolved in Aromatic 150 solvent (4.27 g) to form a second mixture, which was then added to the first mixture with agitation. Finally, surfactants Ethomeen T/15 (1.33 g), Ethomeen C/15 (0.51 g) and Surfonic L12-6 (0.84 g) were added and the whole composition was stirred, using an overhead electric stirrer, under moderate agitation for 30 minutes.

The composition was a clear amber microemulsion that was physically stable at −10° C., room temperature (approximately 22° C.) and 60° C. The microemulsion exhibited good dispersion in water.

Example 3

A microemulsion composition was prepared having the following ingredients:

| | |
|---|---|
| glyphosate IPA salt solution (MON 0139) | 68.29%[1] |
| water | 3.31% |
| 2N hydrochloric acid | 11.53% |
| Solvent (Aromatic 150) | 10.65% |
| carfentrazone-ethyl (91.2% active) | 0.18% |
| Emulsifier (Ethomeen T/15) | 4.36% |
| Emulsifier (Ethomeen C/15) | 0.00% |
| Dispersant (Surfonic L12-6) | 1.67% |

[1]Equivalent to 42.34% glyphosate IPA active ingredient.

MON 0139 (27.42 g) was mixed with water (1.33 g) and 2N hydrochloric acid (4.63 g) to form a first mixture. Carfentrazone-ethyl (0.0740 g) was dissolved in Aromatic 150 solvent (4.28 g) to form a second mixture, which was then added to the first mixture with agitation. Finally, surfactants Ethomeen T/15 (1.75 g) and Surfonic L12-6 (0.67 g) were added and the whole composition was stirred, using an overhead electric stirrer, under moderate agitation for 30 minutes.

The composition was a clear amber microemulsion that was physically stable at −10° C., room temperature (approximately 22° C.) and 60° C. The microemulsion exhibited good dispersion in water.

Example 4

A microemulsion composition was prepared having the following ingredients:

| | |
|---|---|
| glyphosate IPA salt solution (MON 0139) | 67.79%[1] |
| water | 4.10% |
| 2N hydrochloric acid | 11.37% |
| Solvent (Aromatic 150) | 10.57% |
| carfentrazone-ethyl (91.2% active) | 0.18% |
| Emulsifier (Ethomeen T/15) | 4.33% |
| Emulsifier (Ethomeen C/15) | 0.00% |
| Dispersant (Surfonic L12-6) | 1.66% |

[1]Equivalent to 42.03% glyphosate IPA active ingredient.

MON 0139 (27.42 g) was mixed with water (1.66 g) and 2N hydrochloric acid (4.60 g) to form a first mixture. Carfentrazone-ethyl (0.0740 g) was dissolved in Aromatic 150 solvent (4.28 g) to form a second mixture, which was then added to the first mixture with agitation. Finally, surfactants Ethomeen T/15 (1.75 g), and Surfonic L12-6 (0.67 g) were added and the whole composition was stirred, using an overhead electric stirrer, under moderate agitation for 30 minutes.

The composition was a clear amber microemulsion that was physically stable at −10° C., room temperature (approximately 22° C.) and 60° C. The microemulsion exhibited good dispersion in water.

Example 5

A microemulsion composition was prepared having the following ingredients:

| | |
|---|---|
| glyphosate IPA salt solution (MON 0139) | 67.84%[1] |
| water | 2.47% |
| 2N hydrochloric acid | 11.41% |
| Solvent (Aromatic 150) | 12.02% |
| carfentrazone-ethyl (91.2% active) | 0.18% |
| Emulsifier (Ethomeen T/15) | 4.33% |
| Emulsifier (Ethomeen C/15) | 0.00% |
| Dispersant (Surfonic L12-6) | 1.76% |

[1]Equivalent to 42.06% glyphosate IPA active ingredient.

MON 0139 (27.42 g) was mixed with water (1.00 g) and 2N hydrochloric acid (4.61 g) to form a first mixture. Carfentrazone-ethyl (0.0740 g) was dissolved in Aromatic 150 solvent (4.86 g) to form a second mixture, which was then added to the first mixture with agitation. Finally, surfactants Ethomeen T/15 (1.75 g) and Surfonic L12-6 (0.71 g) were added and the whole composition was stirred, using an overhead electric stirrer, under moderate agitation for 30 minutes.

The composition was a clear amber microemulsion that was physically stable at −10° C., room temperature (approximately 22° C.) and 60° C. The microemulsion exhibited good dispersion in water.

Example 6

A microemulsion composition was prepared having the following ingredients:

| | |
|---|---|
| glyphosate IPA salt solution (MON 0139) | 67.71%[1] |
| water | 2.30% |
| 2N hydrochloric acid | 11.43% |
| Solvent (Aromatic 150) | 10.56% |
| carfentrazone-ethyl (91.2% active) | 0.18% |
| Emulsifier (Ethomeen T/15) | 6.27% |
| Sodium chloride | 0.96% |
| Dispersant (Surfonic L12-6) | 0.59% |

[1]Equivalent to 41.98% glyphosate IPA active ingredient.

Sodium chloride (0.39 g) was dissolved in water (0.93 g) and 2N hydrochloric acid (4.63 g) and the resulting solution was mixed with MON 0139 (27.43 g) to form a first mixture. Carfentrazone-ethyl (0.0740 g) was dissolved in Aromatic 150 solvent (4.28 g) to form a second mixture, which was then added to the first mixture with agitation. Finally, surfactants Ethomeen T/15 (2.54 g) and Surfonic L12-6 (0.24 g) were added and the whole composition was stirred, using an overhead electric stirrer, under moderate agitation for 30 minutes.

The composition was a clear amber microemulsion that was physically stable at −10° C., room temperature (approximately 22° C.) and 60° C. The microemulsion exhibited good dispersion in water.

Example 7

A microemulsion composition was prepared having the following ingredients:

| | |
|---|---|
| glyphosate IPA salt solution (MON 0139) | 67.89%[1] |
| water | 1.91% |
| 2N hydrochloric acid | 11.41% |
| Solvent (Aromatic 150) | 12.03% |
| carfentrazone-ethyl (91.2% active) | 0.18% |
| Emulsifier (Ethomeen T/15) | 5.00% |
| Sodium Chloride | 0.40% |
| Dispersant (Surfonic L12-6) | 1.19% |

[1]Equivalent to 42.09% glyphosate IPA active ingredient.

Sodium chloride (0.16 g) was dissolved in water (0.77 g) and 2N hydrochloric acid (4.61 g) and the resulting solution was mixed with MON 0139 (27.43 g) to form a first mixture. Carfentrazone-ethyl (0.0740 g) was dissolved in Aromatic 150 solvent (4.86 g) to form a second mixture, which was then added to the first mixture with agitation. Finally, surfactants Ethomeen T/15 (2.02 g) and Surfonic L12-6 (0.48 g) were added and the whole composition was stirred, using an overhead electric stirrer, under moderate agitation for 30 minutes.

The composition was a clear amber microemulsion that was physically stable at −10° C., room temperature (approximately 22° C.) and 60° C. The microemulsion exhibited good dispersion in water.

Example 8

A microemulsion composition was prepared having the following ingredients:

| | |
|---|---|
| glyphosate IPA salt solution (MON 0139) | 67.82%[1] |
| water | 3.76% |
| 2N hydrochloric acid | 10.39% |
| Solvent (Aromatic 150) | 12.01% |
| carfentrazone-ethyl (91.2% active) | 0.18% |
| Emulsifier (Ethomeen T/15) | 4.01% |
| Sodium Chloride | 0.45% |
| Dispersant (Surfonic L12-6) | 1.39% |

[1]Equivalent to 42.05% glyphosate IPA active ingredient.

Sodium chloride (0.18 g) was dissolved in water (1.52 g) and 2N hydrochloric acid (4.20 g) and the resulting solution was mixed with MON 0139 (27.42 g) to form a first mixture. Carfentrazone-ethyl (0.0740 g) was dissolved in Aromatic 150 solvent (4.86 g) to form a second mixture, which was then added to the first mixture with agitation. Finally, surfactants Ethomeen T/15 (1.62 g) and Surfonic L12-6 (0.56 g) were added and the whole composition was stirred, using an overhead electric stirrer, under moderate agitation for 30 minutes.

The composition was a clear amber microemulsion that was physically stable at −10° C., room temperature (approximately 22° C.) and 60° C. The microemulsion exhibited good dispersion in water.

Example 9

A microemulsion composition was prepared having the following ingredients:

| | |
|---|---|
| glyphosate IPA salt solution (MON 0139) | 67.72%[1] |
| water | 5.39% |
| 2N hydrochloric acid | 10.38% |
| Solvent (Aromatic 150) | 10.56% |
| carfentrazone-ethyl (91.2% active) | 0.18% |
| Emulsifier (Ethomeen T/15) | 4.00% |
| Sodium Chloride | 0.44% |
| Dispersant (Surfonic L12-6) | 1.32% |

[1]Equivalent to 41.99% glyphosate IPA active ingredient.

Sodium chloride (0.18 g) was dissolved in water (2.18 g) and 2N hydrochloric acid (4.20 g) and the resulting solution was mixed with MON 0139 (27.41 g) to form a first mixture. Carfentrazone-ethyl (0.0739 g) was dissolved in Aromatic 150 solvent (4.27 g) to form a second mixture, which was then added to the first mixture with agitation. Finally, surfactants Ethomeen T/15 (1.62 g) and Surfonic L12-6 (0.54 g) were added and the whole composition was stirred, using an overhead electric stirrer, under moderate agitation for 30 minutes.

The composition was a clear amber microemulsion that was physically stable at −10° C., room temperature (approximately 22° C.) and 60° C. The microemulsion exhibited good dispersion in water.

Example 10

A microemulsion composition was prepared having the following ingredients:

| | |
|---|---|
| glyphosate IPA salt solution (MON 0139) | 67.37%[1] |
| ammonium chloride | 1.11% |
| 2N hydrochloric acid | 11.31% |
| Solvent (Aromatic 150) | 11.93% |
| carfentrazone-ethyl (91.2% active) | 0.18% |
| Emulsifier (Ethomeen T/15) | 3.07% |
| Emulsifier (Ethomeen C/15) | 2.95% |
| Dispersant (Surfonic L12-6) | 2.09% |

[1]Equivalent to 41.77% glyphosate IPA active ingredient.

Ammonium chloride (0.11 g) was dissolved in water (1.47 g) and 2N hydrochloric acid (4.60 g) and the resulting solution was mixed with MON 0139 (27.41 g) to form a first mixture. Carfentrazone-ethyl (0.07 g) was dissolved in Aromatic 150 solvent (4.27 g) to form a second mixture, which was then added to the first mixture with agitation. Finally, surfactants Ethomeen T/15 (1.33 g), Ethomeen C/15 (0.51 g) and Surfonic L12-6 (0.84 g) were added and the whole composition was stirred, using an overhead electric stirrer, under moderate agitation for 30 minutes.

The composition was a clear amber microemulsion that was physically stable at −10° C., room temperature (approximately 22° C.) and 50° C. The microemulsion exhibited good dispersion in water.

Example 11

The following example demonstrates the effect of varying the amount of solvent used in the formulation on the stability of carfentrazone-ethyl in compositions of the present invention. All compositions were prepared as in the Examples above using the glyphosate IPA salt solution MON 0139 and carfentrazone-ethyl. The amount and type of solvent was varied as in the following Table 1. For all of the compositions prepared, five aliquots were taken and stored in capped glass bottles. Aliquots were stored at 0° C., Room Temperature (approximately 22° C.), 40° C., 50° C. and 60° C. to accelerate any chemical degradation of the carfentrazone-ethyl that might occur. After storing the aliquots for four weeks (three weeks for the 60° C. samples), carfentrazone-ethyl was assayed by HPLC. Assays were compared with those from the freshly prepared samples of each composition to determine the degree of chemical degradation. Results are shown in Table 1 as percentages of carfentrazone-ethyl remaining. As indicated in the Table, SS 225 represents Sure Sol 225 as the solvent, Ar 150 represents Aromatic 150 as the solvent and Ar 200 represents Aromatic 200 as the selected solvent. Results represented as "--" indicate that no data was available for a particular sample.

TABLE 1

| Solvent Type | SS 225 | SS 225 | SS 225 | SS 225 | Ar 150 | Ar 200 | Ar 150 |
|---|---|---|---|---|---|---|---|
| % Solvent | 1.5 | 3.2 | 6.6 | 8.3 | 8.3 | 8.3 | 10.3 |
| 0° C. | 94 | 93 | 94 | 98 | 99 | 100 | 100 |

TABLE 1-continued

| Solvent Type | SS 225 | SS 225 | SS 225 | SS 225 | Ar 150 | Ar 200 | Ar 150 |
|---|---|---|---|---|---|---|---|
| Room Temp. | 90 | 90 | 92 | 97 | 99 | 99 | 100 |
| 40° C. | 50 | 63 | 80 | 87 | 98 | 96 | 92 |
| 50° C. | — | — | — | — | — | 92 | 92 |
| 60° C. | — | — | — | — | — | 90 | 90 |

Example 12

This example demonstrates the effect of compositions of the invention for controlling broadleaf weeds and grasses. Test were conducted by preparing a microemulsion composition (Formulation MON 78402) as in Example 1 having the following ingredients:

| | |
|---|---|
| glyphosate IPA salt solution (MON 0139) | 67.80% |
| ammonium chloride/sodium chloride | 1.53% |
| 2N hydrochloric acid | 10.39% |
| Solvent (Aromatic 150/200) | 10.57% |
| carfentrazone-ethyl (91.2% active) | 0.18% |
| Emulsifiers (Ethomeen T/15 and C/15) | 6.06% |
| Dispersant (Surfonic L12-6) | 1.58% |

The microemulsion composition was applied to a field (1.0 lb a.i./a) having 4–8 inch weeds actively growing. As a comparison, a separate field test was conducted wherein 0.25% of non-ionic surfactant was added to the microemulsion composition MON 78402 and applied to a field (1.0 lb a.i./a). The formulations were applied to the field using a $CO_2$ backpack with 3 replications per treatment at a spray volume of 10 gallons per acre. Burndown was evaluated at 2 to 4 days after treatment with a final control evaluation at 21 to 28 days after treatment.

The test was evaluated for control of broadleaf weeds and grasses in comparison to standard burndown data for formulations of Roundup® Ultra brand herbicide comprising glyphosate IPA salt as the only herbicidal active ingredient. Broadleaf weed species evaluated included p. lettuce, mustard, w. mustard, f. pennycress, dandelion, c. chickweed, sowthistle, c. primrose, w. buckwheat, henbit, cidweed, c. geranium, horseweed, bittercress, shepardspurse, velvetleaf, r. thistle, p. sida, h. sesbania, p. smartweed, kochia, morninglory, lambsquarter, g. ragweed, c. waterhemp, pigweed, and sicklepod. Grass species evaluated included annual bluegrass, italian ryegrass, barnyardgrass, downy bromegrass and foxtail. Effects on glyphosate-tolerant crops such as Roundup®-ready corn, soybeans and cotton were also evaluated. Results are presented in Tables 2 and 3 below as percentage enhancement over standard applications of Roundup® Ultra brand herbicide. Table 2 includes results for the early evaluation at 2 to 4 days after treatment and Table 3 presents results for the final evaluation at 21 to 28 days after treatment.

Results represented as "--" indicate that no data was available for a particular sample.

TABLE 2

| | MON 78402 | MON 78402 + NIS |
|---|---|---|
| Winter Weeds | | |
| P. Lettuce | 15 | — |
| Mustard | — | 35 |
| W. Mustard | 5 | — |
| F. Pennycress | 10 | — |
| Dandelion | 20 | — |
| C. Chickweed | -2 | — |
| Sowthistle | 21 | 20 |
| C. Primrose | 8 | 5 |
| W. Buckwheat | 0 | -8 |
| Henbit | 4 | 9 |
| Cudweed | 4 | — |
| C. Geranium | 6 | 9 |
| Horseweed | — | — |
| Bittercress | 10 | 12 |
| Shepardspurse | 24 | 20 |
| Filaree | 26 | — |
| Spring/Summer Weeds | | |
| Velvetleaf | 41 | 33 |
| R. Thistle | 0 | 30 |
| P. Sida | 13 | 15 |
| H. Sesbania | -5 | -7 |
| P. Smartweed | 12 | 25 |
| Kochia | 0 | 15 |
| Morninglory | 37 | 30 |
| Lambsquarter | 27 | 25 |
| G. Ragweed | — | 52 |
| C. Waterhemp | — | 24 |
| Pigweed | 9 | — |
| Sicklepod | 1 | 3 |
| Annual Grasses | | |
| Annual Bluegrass | 5 | — |
| Italian Ryegrass | 0 | — |
| Barnyardgrass | -1 | -1 |
| Downy Bromegrass | -2 | 0 |
| Foxtail | 3 | 7 |
| Roundup ®-ready Crops | | |
| RR-Corn | 5 | 9 |
| RR-Soybeans | 31 | 25 |
| RR-Cotton | 50 | 40 |

TABLE 3

| | MON 78402 | MON 78402 + NIS |
|---|---|---|
| Winter Weeds | | |
| P. Lettuce | 7 | — |
| Mustard | — | 35 |
| W. Mustard | 1 | — |
| F. Pennycress | 4 | — |
| Dandelion | -15 | — |
| C. Chickweed | 0 | — |
| Sowthistle | -1 | 1 |
| C. Primrose | -1 | 12 |
| W. Buckwheat | 3 | 4 |
| Henbit | -3 | 2 |
| Cudweed | 0 | — |
| C. Geranium | 12 | — |
| Horseweed | — | — |
| Bittercress | 0 | 0 |
| Shepardspurse | 7 | 13 |
| Filaree | -15 | — |
| Spring/Summer Weeds | | |
| Velvetleaf | 8 | 3 |
| R. Thistle | — | -12 |
| P. Sida | -5 | 0 |

TABLE 3-continued

|  | MON 78402 | MON 78402 + NIS |
|---|---|---|
| H. Sesbania | 3 | 3 |
| P. Smartweed | −4 | −3 |
| Kochia | 0 | −7 |
| Morninglory | 15 | 17 |
| Lambsquarter | −3 | −4 |
| G. Ragweed | — | −7 |
| C. Waterhemp | — | — |
| Pigweed | 0 | 0 |
| Sicklepod | −3 | −2 |
| Annual Grasses |  |  |
| Annual Bluegrass | 5 | — |
| Italian Ryegrass | 0 | — |
| Barnyardgrass | −1 | −1 |
| Downy Bromegrass | −2 | 0 |
| Foxtail | 3 | 7 |
| Roundup ®-ready Crops |  |  |
| RR-Corn | 5 | 9 |
| RR-Soybeans | 31 | 25 |
| RR-Cotton | 50 | 40 |

Example 13

A microemulsion composition (MON 78481) was prepared having the following composition:

| glyphosate potassium salt solution (MON 78623) | 76.27%[1] |
|---|---|
| sodium chloride | 0.36% |
| phosphoric acid | 2.87% |
| Solvent (Aromatic 150) | 10.38% |
| carfentrazone-ethyl (92.2% active) | 0.21% |
| Emulsifier (Ethomeen T/15) | 1.98% |
| Emulsifier (Ethomeen C/12) | 2.03% |
| Dispersant (Surfonic L12-6) | 1.57% |
| Water | 4.31% |
| Dye (Yellow) | 0.01% |

[1]47.90% glyphosate acid equivalent

Sodium chloride (45.5 g) was dissolved in water (542.5 g) and phosphoric acid (360.5 g) and the resulting solution was mixed with MON 78623 (9591.0 g) to form a first mixture. Carfentrazone-ethyl (26.6 g) was dissolved in Aromatic 150 (1305.6 g) to form a second mixture, which was then added to the first mixture with agitation. Finally, surfactants Ethomeen T/15 (248.5 g), Ethomeen C/12 (255.5 g) and Surfonic L12-6 (197.5 g) were added and the whole composition was stirred, using an overhead electric stirrer, under moderate agitation for 30 minutes.

The composition was a clear amber microemulsion that was physically stable at 10° C., room temperature (approximately 22° C.) and 60° C. The microemulsion exhibited good dispersion in water.

Example 14

A microemulsion composition (MON 78482) was prepared having the following composition:

| glyphosate potassium salt solution (47.8% a.e.) | 76.56%[1] |
|---|---|
| sodium chloride | 0.42% |
| phosphoric acid | 2.88% |
| Solvent (Aromatic 150) | 10.51% |
| carfentrazone-ethyl (92.2% active) | 0.11% |
| Emulsifier (Ethomeen T/15) | 1.98% |
| Emulsifier (Ethomeen C/12) | 2.01% |
| Dispersant (Surfonic L12-6) | 1.34% |
| Water | 4.19% |

[1]47.80% glyphosate acid equivalent

Sodium chloride (0.15 g) was dissolved in water (1.50 g) and phosphoric acid (1.03 g). The resulting solution was mixed with a potassium glyphosate salt solution (27.40 g) comprising 47.80% glyphosate active ingredient to form a first mixture. Carfentrazone-ethyl (0.04 g) was dissolved in Aromatic 150 (3.76 g) to form a second mixture, which was then added to the first mixture with agitation. Finally, surfactants Ethomeen T/15 (0.71 g), Ethomeen C/12 (0.72 g) and Surfonic L12-6 (0.48 g) were added and the whole composition was stirred, using an overhead electric stirrer, under moderate agitation for 30 minutes.

The composition was a clear amber microemulsion that was physically stable at −10° C., room temperature (approximately 22° C.) and 60° C. The microemulsion exhibited good dispersion in water.

The preceding description of specific embodiments of the present invention is not intended to be a complete list of every possible embodiment of the invention. Persons skill in this will recognize that modifications can be made to the specific embodiments described here that would be within the scope of the present invention.

What is claimed:

1. A liquid concentrate herbicidal microemulsion composition having a continuous aqueous phase and a discontinuous oil phase, the composition comprising:

(i) an herbicide comprising N-(phosphonomethyl)glycine or a salt thereof in said aqueous phase, the N-(phosphonomethyl)glycine being present in a concentration that is biologically effective when the composition is diluted in a suitable volume of water and applied to the foliage of a susceptible plant;

(ii) an herbicide comprising carfentrazone-ethyl in said oil phase, the carfentrazone-ethyl being present in a concentration that is biologically effective when the composition is diluted in a suitable volume of water and applied to the foliage of a susceptible plant;

(iii) at least one emulsifying agent having a tertiary amine functionality, the emulsifying agent being present in a concentration sufficient to provide acceptable physical stability of the microemulsion; and (iv) a substantially water-immiscible organic solvent in said oil phase, wherein the organic solvent is selected such that the carfentrazone-ethyl herbicide has an organic solvent/water partition coefficient, expressed as a logarithm, of about 4 or greater.

2. An emulsion composition having a continuous aqueous phase and a discontinuous oil phase, the composition comprising:

(i) N-(phosphonomethyl)glycine or a salt thereof dissolved in said aqueous phase, the N-(phosphonomethyl)glycine being present in a concentration that is biologically effective when the composition is diluted in a suitable volume of water and applied to the foliage of a susceptible plant;

(ii) carfentrazone-ethyl in said oil phase, the carfentrazone-ethyl being present in a concentration that is biologically effective when the composition is diluted in a suitable volume of water and applied to the foliage of a susceptible plant;

(iii) a substantially water-immiscible organic solvent in said oil phase, wherein the organic solvent is selected such that the carfentrazone-ethyl has an organic solvent/water partition coefficient, expressed as a logarithm, of about 4 or greater;

(iv) a water-soluble chloride salt or hydrochloric acid present in a concentration sufficient to inhibit substantial degradation of the carfentrazone-ethyl; and (v) one or more surfactants present in a concentration sufficient to provide acceptable physical stability of the emulsion, and provide acceptable dispersion of the emulsion upon dilution thereof in a suitable volume of water for application to plants.

3. A composition as set forth in claim 2 wherein the weight ratio of organic solvent to carfentrazone-ethyl herbicide ranges from about 3:1 to about 75:1.

4. A composition as set forth in claim 2 wherein the weight ratio of organic solvent to carfentrazone-ethyl herbicide ranges from about 3:1 to about 60:1.

5. A composition as set forth in claim 2 wherein the weight ratio of organic solvent to carfentrazone-ethyl herbicide ranges from about 5:1 to about 50:1.

6. A composition as set forth in claim 2 wherein the organic solvent is an aromatic solvent.

7. A composition as set forth in claim 2 wherein the organic solvent is selected such that the carfentrazone-ethyl herbicide has an organic solvent/water partition coefficient, expressed as a logarithm, of at least about 5 or greater.

8. A composition as set forth in claim 1 further comprising a stabilizing agent present in a concentration sufficient to inhibit substantial degradation of the carfentrazone-ethyl herbicide.

9. A composition as set forth in claim 8 wherein the stabilizing agent is one or more water soluble chloride(s) selected from the group consisting of hydrochloric acid, alkali metal chlorides, ammonium chloride, low molecular weight organic ammonium chlorides, and a quaternary ammonium chloride surfactants.

10. A composition as set forth in claim 9 wherein the stabilizing agent is present in a concentration sufficient to provide a concentration of chloride ion of from about 0.5% to about 2.5% by weight.

11. A composition as set forth in claim 9 wherein the stabilizing agent is ammonium chloride, sodium chloride, hydrochloric acid or a combination thereof.

12. A composition as set forth in claim 1 wherein the combined concentration of N-(phosphonomethyl)glycine herbicide and carfentrazone-ethyl herbicide ranges from about 5% to about 50% by weight of the composition.

13. A composition as set forth in claim 1 wherein the combined concentration of N-(phosphonomethyl)glycine herbicide and carfentrazone-ethyl herbicide ranges from about 20% to about 50% by weight of the composition.

14. A composition as set forth in claim 1 wherein the weight ratio of N--(phosphonomethyl)glycine herbicide to carfentrazone-ethyl herbicide ranges from about 190:1 to about 1:1.

15. A composition as set forth in claim 1 wherein the total concentration of all surfactants present in the composition is less than about 12% by weight.

16. A composition as set forth in claim 1 wherein the emulsifying agent(s) comprises one or more surfactants selected from the group consisting of polyoxyethylene (2–20) tertiary alkylamines and polyoxyethylene (2–20) tertiary alkyletheramines.

17. A composition as set forth in claim 16 wherein said alkylamines and alkyletheramines have alkyl chains having from about 12 to about 18 carbon atoms.

18. A composition as set forth in claim 16 wherein said alkylamine and/or alkyletheramine surfactant(s) comprise about 3% to about 10% by weight of the composition.

19. A composition as set forth in claim 1 wherein the aqueous phase has a pH that is minimally conducive to chemical degradation of the N-(phosphonomethyl)glycine herbicide.

20. A composition as set forth in claim 1 further comprising one or more dispersing agents present in a concentration sufficient to provide acceptable dispersion of the microemulsion upon dilution thereof in a suitable volume of water, but not sufficient to substantially destabilize the microemulsion prior to such dilution.

21. A composition as set forth in claim 20 wherein the dispersing agent is one or more nonionic surfactants selected from the group consisting of polyoxyethylene (2–20) alkylethers and polyoxyethylene (2–20) alkylphenylethers.

22. A composition as set forth in claim 20 wherein the nonionic surfactant(s) is present in a concentration of about 0.5% to about 3% by weight of the composition.

23. A process for controlling the growth of or killing unwanted plants, the process comprising:

diluting a liquid concentrate herbicidal microemulsion composition of claim 1 in a suitable volume of water to form a plant treatment composition; and, applying said plant treatment composition to the foliage of said unwanted plants.

24. A liquid herbicidal microemulsion composition, the composition comprising:

(i) a continuous aqueous phase comprising N-(phosphonomethyl)glycine or a salt thereof, said N-(phosphonomethyl)glycine being present in a concentration that is biologically effective when the composition is diluted in a suitable volume of water and applied to the foliage of a susceptible plant;

(ii) a discontinuous oil phase comprising carfentrazone-ethyl in a substantially water-immiscible organic solvent, said carfentrazone-ethyl being present in a concentration that is biologically effective when the composition is diluted in a suitable volume of water and applied to the foliage of a susceptible plant;

(iii) at least one emulsifying agent having a tertiary amine functionality, said emulsifying agent being present in a concentration sufficient to provide acceptable physical stability of said microemulsion;

(iv) a stabilizing agent present in a concentration sufficient to inhibit substantial degradation of said carfentrazone-ethyl; and (v) one or more surfactants present in a concentration sufficient to provide acceptable physical stability of the emulsion, and provide acceptable dispersion of the emulsion upon dilution thereof in a suitable volume of water for application to plants.

25. A composition as set forth in claim 24 wherein the organic solvent is selected such that the carfentrazone-ethyl has an organic solvent/water partition coefficient, expressed as a logarithm, of about 4 or greater.

26. A composition as set forth in claim 25 wherein the weight ratio of organic solvent to carfentrazone-ethyl ranges from about 3:1 to about 75:1.

27. A composition as set forth in claim 25 wherein the weight ratio of organic solvent to carfentrazone-ethyl ranges from about 3:1 to about 60:1.

28. A composition as set forth in claim 25 wherein the weight ratio of organic solvent to carfentrazone-ethyl ranges from about 5:1 to about 50:1.

29. A composition as set forth in claim 25 wherein the organic solvent is an aromatic solvent.

30. A composition as set forth in claim 24 wherein the organic solvent is selected such that the carfentrazone-ethyl has an organic solvent/water partition coefficient, expressed as a logarithm, of at least about 5 or greater.

31. A composition as set forth in claim 24 wherein the stabilizing agent is one or more water soluble chloride(s) selected from the group consisting of hydrochloric acid, alkali metal chlorides, ammonium chloride, low molecular weight organic ammonium chlorides, and a quaternary ammonium chloride surfactants.

32. A composition as set forth in claim 31 wherein the stabilizing agent is present in a concentration sufficient to provide a concentration of chloride ion of from about 0.5% to about 2.5% by weight.

33. A composition as set forth in claim 31 wherein the stabilizing agent is ammonium chloride, sodium chloride, hydrochloric acid or a combination thereof.

34. A composition as set forth in claim 24 wherein the combined concentration of N-(phosphonomethyl)glycine and carfentrazone-ethyl ranges from about 5% to about 50% by weight of the composition.

35. A composition as set forth in claim 24 wherein the combined concentration of N-(phosphonomethyl)glycine and carfentrazone-ethyl ranges from about 20% to about 50% by weight of the composition.

36. A composition as set forth in claim 24 wherein the weight ratio of N-(phosphonomethyl)glycine to carfentrazone-ethyl ranges from about 190:1 to about 1:1.

37. A composition as set forth in claim 24 wherein the total concentration of all surfactants present in the composition is less than about 12% by weight.

38. A composition as set forth in claim 24 wherein the emulsifying agent(s) comprises one or more surfactants selected from the group consisting of polyoxyethylene (2–20) tertiary alkylamines and polyoxyethylene (2–20) tertiary alkyletheramines.

39. A composition as set forth in claim 38 wherein said alkylamines and alkyletheramines have alkyl chains having from about 12 to about 18 carbon atoms.

40. A composition as set forth in claim 38 wherein said alkylamine and/or alkyletheramine surfactant(s) comprise about 3% to about 10% by weight of the composition.

41. A composition as set forth in claim 24 wherein the aqueous phase has a pH that is minimally conducive to chemical degradation of the N-(phosphonomethyl)glycine.

42. A composition as set forth in claim 24 wherein said surfactants comprise one or more nonionic surfactants selected from the group consisting of polyoxyethylene (2–20) alkylethers and polyoxyethylene (2–20) alkylphenylethers.

43. A composition as set forth in claim 42 wherein said surfactants are present in a concentration of about 0.5% to about 3% by weight of the composition.

44. An emulsion composition having a continuous aqueous phase and a discontinuous oil phase, the composition comprising:

(i) N-(phosphonomethyl)glycine or a salt thereof dissolved in said aqueous phase, the N-(phosphonomethyl)glycine being present in a concentration that is biologically effective when the composition is diluted in a suitable volume of water and applied to the foliage of a susceptible plant;

(ii) carfentrazone-ethyl in said oil phase, the carfentrazone-ethyl being present in a concentration that is biologically effective when the composition is diluted in a suitable volume of water and applied to the foliage of a susceptible plant;

(iii) at least one emulsifying agent having a tertiary amine functionality present in a concentration sufficient to provide acceptable physical stability of said emulsion;

(iv) a substantially water-immiscible organic solvent in said oil phase;

(v) a water-soluble chloride salt or hydrochloric acid present in a concentration sufficient to inhibit substantial degradation of the carfentrazone-ethyl; and (vi) one or more surfactants present in a concentration sufficient to provide acceptable physical stability of the emulsion, and provide acceptable dispersion of the emulsion upon dilution thereof in a suitable volume of water for application to plants.

45. A composition as set forth in claim 44 wherein the emulsion is a suspoemulsion, microemulsion, or macroemulsion.

* * * * *

UNITED STATES PATENT AND TRADEMARK OFFICE
CERTIFICATE OF CORRECTION

PATENT NO.   : 6,689,719 B2
DATED        : February 10, 2004
INVENTOR(S)  : Ganiyu A. Jimoh It is certified that error appears in the above-identified patent and that said Letters Patent is hereby corrected as shown below:

Title page,
Item [54], Title, reads "COFORMULATION OF CARFENTRAZONE-ETHYL AND GLYPHASATE" and should read -- COFORMULATION OF CARFENTRAZONE-ETHYL AND A WATER-SOLUBLE HERBICIDE --.

Signed and Sealed this

Third Day of August, 2004

JON W. DUDAS
*Acting Director of the United States Patent and Trademark Office*